United States Patent [19]
Dean et al.

[11] Patent Number: 6,113,878
[45] Date of Patent: *Sep. 5, 2000

[54] TECHNETIUM-99M LABELED PEPTIDES FOR IMAGING

[75] Inventors: Richard T. Dean; John Lister-James, both of Bedford, N.H.

[73] Assignee: Diatide, Inc., Londonderry, N.H.

[*] Notice: This patent is subject to a terminal disclaimer.

[21] Appl. No.: 08/467,567

[22] Filed: Jun. 6, 1995

Related U.S. Application Data

[62] Division of application No. 07/893,981, Jun. 5, 1992, Pat. No. 5,508,020.

[51] Int. Cl.[7] .............................. A61K 51/00; A61M 36/14
[52] U.S. Cl. ................ 424/1.69; 424/1.11; 424/1.65; 530/300; 530/324; 530/325; 530/326; 530/327; 530/328; 530/329; 530/330; 534/14
[58] Field of Search ................. 424/1.11, 1.69, 424/9.1, 1.65; 530/300, 324–330; 534/10, 14, 15

[56] References Cited

U.S. PATENT DOCUMENTS

| | | | |
|---|---|---|---|
| 4,434,151 | 2/1984 | Byrne et al. | 424/1.1 |
| 4,444,690 | 4/1984 | Fritzberg et al. | 260/429 |
| 4,571,430 | 2/1986 | Bryne et al. | 560/148 |
| 4,575,556 | 3/1986 | Byrne et al. | 549/63 |
| 4,647,447 | 3/1987 | Gries et al. | 424/9.36 |
| 4,673,562 | 6/1987 | Davison et al. | 424/1.1 |
| 4,832,940 | 5/1989 | Ege | 424/1.1 |
| 4,861,869 | 8/1989 | Nicolotti et al. | 530/402 |
| 4,965,392 | 10/1990 | Fritzberg et al. | 558/254 |
| 4,988,496 | 1/1991 | Srinivasan et al. | 424/1.11 |
| 5,061,641 | 10/1991 | Shochat et al. | 424/1.49 |
| 5,180,816 | 1/1993 | Dean | 530/404 |
| 5,196,510 | 3/1993 | Rodwell | 424/1.1 X |
| 5,225,180 | 7/1993 | Dean et al. | 424/1.1 |
| 5,273,743 | 12/1993 | Ahlem et al. | 424/1.53 |
| 5,508,020 | 4/1996 | Dean et al. | 424/1.69 |

FOREIGN PATENT DOCUMENTS

| | | |
|---|---|---|
| 453082 | 10/1990 | European Pat. Off. |
| WO8910759 | 11/1989 | WIPO |
| WO8912625 | 12/1989 | WIPO |
| WO 90/03798 | 4/1990 | WIPO |
| WO9010463 | 9/1990 | WIPO |
| WO9101144 | 2/1991 | WIPO |
| WO9119739 | 12/1991 | WIPO |
| WO9205154 | 4/1992 | WIPO |
| WO9213572 | 8/1992 | WIPO |
| 9323085 | 11/1993 | WIPO |
| WO9321962 | 11/1993 | WIPO |
| 9325244 | 12/1993 | WIPO |
| 9407918 | 4/1994 | WIPO |
| 9423758 | 10/1994 | WIPO |
| 9529708 | 11/1995 | WIPO |
| 9533496 | 12/1995 | WIPO |

OTHER PUBLICATIONS

Zubay, Geoffrey (1983), Biochemistry, "Protein Structure and Function" pp. 3–7.

*Primary Examiner*—Jose' G. Dees
*Assistant Examiner*—Dameron Jones
*Attorney, Agent, or Firm*—Patricia A. McDaniels; Kevin E. Noonan

[57] ABSTRACT

This invention relates to radiolabeled peptides and methods for producing such peptides. Specifically, the invention relates to peptides, methods and kits for making such peptides, and methods for using such peptides to image sites in a mammalian body labeled with technetium-99m (Tc-99m) via Tc-99m binding moieties. In particular, the peptide reagents of the invention are covalently linked to a polyvalent linker moiety, so that the polyvalent linker moiety is covalently linked to a multiplicity of the specific-binding peptides, and the Tc-99m binding moieties are covalently linked to a plurality of the specific-binding peptides, the polyvalent linker moiety, or to both the specific-binding peptides and the polyvalent linker moiety.

22 Claims, No Drawings

TECHNETIUM-99M LABELED PEPTIDES FOR IMAGING

This is a divisional of application Ser. No. 07/893,981 filed Jun. 5, 1992 now U.S. Pat. No. 5,508,020.

BACKGROUND OF THE INVENTION

1. Field of the Invention

This invention relates to radiodiagnostic reagents and peptides, and methods for producing labeled radiodiagnostic agents. Specifically, the invention relates to specific-binding peptides, methods and kits for making such peptides, and methods for using such peptides to image sites in a mammalian body labeled with technetium-99m (Tc-99m) via a radiolabel-binding moiety which forms a complex with Tc-99m. In particular, the peptide reagents of the invention are covalently linked to a polyvalent linker moiety, so that the polyvalent linker moiety is covalently linked to a multiplicity of the specific-binding peptides, and the Tc-99m binding moieties are covalently linked to a plurality of the specific-binding peptides, the polyvalent linker moiety, or to both the specific-binding peptides and the polyvalent linker moiety.

2. Description of the Prior Art

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. Tc-99m is a preferred radionuclide because it emits gamma radiation at 140 keV, it has a physical half-life of 6 hours, and it is readily available on-site using a molybdenum-99/technetium-99m generator.

The sensitivity of imaging methods using radioactively-labeled peptides is much higher than other radiopharmaceuticals known in the art, since the specific binding of the radioactive peptide concentrates the radioactive signal over the area of interest. Small synthetic peptides that bind specifically to targets of interest may be advantageously used as the basis for radiotracers. This is because: 1. they may be synthesized chemically (as opposed to requiring their production in a biological system such as bacteria or mammalian cells, or their isolation from a biologically-derived substance such as a fragment of a protein); 2. they are small, hence non-target bound radiotracer is rapidly eliminated from the body, thereby reducing background (non-target) radioactivity and allowing good definition of the target; and 3. small peptides may be readily manipulated chemically to optimize their affinity for a particular binding site.

Small readily synthesized labeled peptide molecules are preferred as routinely-used radiopharmaceuticals. There is clearly a need for small synthetic labeled peptides that can be directly injected into a patient and will image pathological sites by localizing at such sites. Tc-99m labeled small synthetic peptides offer clear advantages as radiotracers for gamma scintigraphy, due to the properties of Tc-99m as a radionuclide for imaging and the utility of specific-binding small synthetic peptides as radiotracer molecules.

Radiolabeled peptides have been reported in the prior art.

Ege et al., U.S. Pat. No. 4,832,940 teach radiolabeled peptides for imaging localized T-lymphocytes.

Olexa et al., 1982, European Patent Application No. 823017009 disclose a pharmaceutically acceptable radiolabeled peptide selected from Fragment $E_1$ isolated from cross-linked fibrin, Fragment $E_2$ isolated from cross-linked fibrin, and peptides having an amino acid sequence intermediate between Fragments $E_1$ and $E_2$.

Ranby et al., 1988, PCT/US88/02276 disclose a method for detecting fibrin deposits in an animal comprising covalently binding a radiolabeled compound to fibrin.

Hadley et al., 1988, PCT/US88/03318 disclose a method for detecting a fibrin-platelet clot in vivo comprising the steps of (a) administering to a patient a labeled attenuated thrombolytic protein, wherein the label is selectively attached to a portion of the thrombolytic protein other than the fibrin binding domain; and (b) detecting the pattern of distribution of the labeled thrombolytic protein in the patient.

Lees et al., 1989, PCT/US89/01854 teach radiolabeled peptides for arterial imaging.

Sobel, 1989, PCT/US89/02656 discloses a method to locate the position of one or more thrombi in an animal using radiolabeled, enzymatically inactive tissue plasminogen activator.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Maraganore et al., 1991, PCT/US90/04642 disclose a radiolabeled thrombus inhibitor comprising (a) a inhibitor moiety; (b) a linker moiety; and (c) and anion binding site moiety.

Rodwell et al., 1991, PCT/US91/03116 disclose conjugates of "molecular recognition units" with "effector domains".

Tubis et al., 1968, Int. J. Appl. Rad. Isot. 19: 835–840 describe labeling a peptide with technetium-99m.

Sundrehagen, 1983, Int. J. Appl. Rad. Isot. 34: 1003 describes labeling polypeptides with technetium-99m.

The use of chelating agents for radiolabeling polypeptides, and methods for labeling peptides and polypeptides with Tc-99m are known in the prior art and are disclosed in co-pending U.S. patent applications Ser. Nos. 07/653,012, 07/807,062, 07/851,074, and 07/871,282, which are hereby incorporated by reference.

Although optimal for radioimaging, the chemistry of Tc-99m has not been as thoroughly studied as the chemistry of other elements and for this reason methods of radiolabeling with technetium are not abundant. Tc-99m is normally obtained as Tc-99m pertechnetate (TcO$_4$; technetium in the +7 oxidation state), usually from a molybdenum-99/technetium-99m generator. However, pertechnetate does not bind well to other compounds. Therefore, in order to radiolabel a peptide, Tc-99m pertechnetate must be converted to another form. Since technetium does not form a stable ion in aqueous solution, it must be held in such solutions in the form of a coordination complex that has sufficient kinetic and thermodynamic stability to prevent decomposition and resulting conversion of Tc-99m either to insoluble technetium dioxide or back to pertechnetate.

For the purpose of radiolabeling, it is particularly advantageous for the Tc-99m complex to be formed as a chelate in which all of the donor groups surrounding the technetium ion are provided by a single chelating ligand. This allows the chelated Tc-99m to be covalently bound to a peptide through a single linker between the chelator and the peptide.

These ligands are sometimes referred to as bifunctional chelating agents having a chelating portion and a linking portion. Such compounds are known in the prior art.

Byrne et al., U.S. Pat, No. 4,434,151 describe homocysteine thiolactone-derived bifunctional chelating agents that can couple radionuclides to terminal amino-containing compounds that are capable of localizing in an organ or tissue to be imaged.

Fritzberg, U.S. Pat. No. 4,444,690 describes a series of technetium-chelating agents based on 2,3-bis(mercaptoacetamido) propanoate.

Byrne et al., U.S. Pat. Nos. 4,571,430 describe novel homocysteine thiolactone bifunctional chelating agents for chelating radionuclides that can couple radionuclides to terminal amino-containing compounds that are capable of localizing in an organ or tissue to be imaged.

Byrne et al., U.S. Pat. Nos. 4,575,556 describe novel homocysteine thiolactone bifunctional chelating agents for chelating radionuclides that can couple radionuclides to terminal amino-containing compounds that are capable of localizing in an organ or tissue to be imaged.

Davison et al., U.S. Pat. No. 4,673,562 describe technetium chelating complexes of bisamido-bisthio-ligands and salts thereof, used primarily as renal function monitoring agents.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Fritzberg et al., European Patent Application No. 86100360.6 describe dithiol, diamino, or diamidocarboxylic acid or amine complexes useful for making technetium-labeled imaging agents.

Dean et al., 1989, PCT/US89/02634 describe bifunctional coupling agents for radiolabeling proteins and peptides.

Flanagan et al., European Patent Application No. 90306428.5 disclose Tc-99m labeling of synthetic peptide fragments via a set of organic chelating molecules.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Dean, co-pending U.S. patent application Ser. No. 07/653,012 teaches reagents and methods for preparing peptides comprising a Tc-99m chelating group covalently linked to a specific binding peptide for radioimaging in vivo, and is hereby incorporated by reference.

Baidoo & Lever, 1990, Bioconjugate Chem. 1: 132–137 describe a method for labeling biomolecules using a bisamine bisthiol group that gives a cationic technetium complex.

It is possible to radiolabel a peptide by simply adding a thiol-containing moiety such as cysteine or mercaptoacetic acid. Such procedures have been described in the prior art.

Schochat et al., U.S. Pat. No. 5,061,641 disclose direct radiolabeling of proteins comprised of at least one "pendent" sulfhydryl group.

Dean et al., co-pending U.S. patent application Ser. No. 07/807,062 teach radiolabeling peptides via attached groups containing free thiols, and is incorporated herein by reference.

Goedemans et al., PCT Application No. WO 89/07456 describe radiolabeling proteins using cyclic thiol compounds, particularly 2-iminothiolane and derivatives.

Thornback et al., EPC Application No. 90402206.8 describe preparation and use of radiolabeled proteins or peptides using thiol-containing compounds, particularly 2-iminothiolane.

Stuttle, PCT Application No. WO 90/15818 describes Tc-99m labeling of RGD-containing oligopeptides.

Although it is possible to label specific-binding peptides with Tc-99m (as disclosed in co-pending U.S. patent applications Ser. No. 07/053,012, now abandoned, which issued as U.S. Pat. No. 5,654,272; Ser. No. 07/807,026, now U.S. Pat. No. 5,443,815; Ser. No. 07/851,074, now abandoned, which issued as U.S. Pat. No. 5,711,931; and Ser. No. 07/871,282, a divisional of which issued as U.S. Pat. No. 5,720,934, all of which are incorporated by reference), some such peptides exhibit low binding site affinity whereby the strength of peptide binding to the target site is insufficient to allow enough of the radioisotope to localize at the targeted site and form a radioimage. Peptides comprised of linear arrays of specific binding peptide repeating units have been described in the prior art. However, alternative arrangements of specific binding peptide units may be preferable in some cases.

Rodwell et al., 1991, PCT/US91/03116 disclose linear arrays of the peptide sequence RGD.

The present invention provides reagents comprised of a multiplicity of specific-binding peptide moieties, having an affinity for targeted sites in vivo sufficient to produce a scintigraphically-detectable image. The incorporation of a multiplicity of specific-binding peptide moieties in the reagents of the invention permits the use of specific binding peptides whose individual binding affinity would not otherwise be sufficient to produce a scintigraphically-detectable image in vivo. In other cases, an improvement in the scintigraphic image produced by a particular specific-binding peptide is achieved using the reagents of this invention.

SUMMARY OF THE INVENTION

The present invention provides reagents useful in preparing radioimaging agents comprising a multiplicity of specific-binding peptide moieties covalently linked to a polyvalent linker moiety, wherein technetium-99m binding moieties are covalently linked to the specific-binding peptides, the polyvalent linker moiety, or to both the specific-binding peptides and the polyvalent linker moieties.

The invention also provides Tc-99m labeled scintigraphic imaging agents prepared from such peptide reagents. The specific-binding peptides of the invention are comprised of peptides that specifically bind to a target in vivo.

In a first aspect of the present invention, the invention provides reagents comprising a multiplicity of specific binding peptides capable of being Tc-99m labeled for imaging sites within a mammalian body, comprising a specific binding peptide having an amino acid sequence of 3–100 amino acids, covalently linked to a polyvalent linking moiety, and Tc-99m binding moieties covalently linked to a plurality of the specific-binding peptides, the polyvalent linker moiety, or both. Preferred embodiments of the invention comprise linear and cyclic specific binding peptides.

In a second aspect, the present invention provides reagents capable of being Tc-99m labeled for imaging sites within a mammalian body, comprising a multiplicity of specific binding peptide having an amino acid sequence of 3–100 amino acids, covalently linked to a polyvalent linking moiety, and a Tc-99m binding moiety covalently linked to a plurality of the specific-binding peptides, the polyvalent linker moiety, or both, wherein the Tc-99m binding moiety has formula:

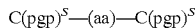

C(pgp)$^S$—(aa)—C(pgp)$^S$ wherein C(pgp)$^S$ is a protected cysteine and (aa) is an amino acid. In a preferred embodiment, the amino acid is glycine. In a preferred embodiment, the peptide comprises between 3 and 30 amino acids. Preferred embodiments of the invention comprise linear and cyclic specific binding peptides.

In a third embodiment, the invention provides reagents capable of being Tc-99m labeled for imaging sites within a mammalian body, comprising a multiplicity of specific binding peptides having an amino acid sequence of 3–100 amino acids, covalently linked to a polyvalent linking moiety, and a Tc-99m binding moiety covalenty linked to a plurality of the specific-binding peptides, the polyvalent linker moiety, or both, wherein the Tc-99m binding moiety comprises a single thiol moiety having the formula:

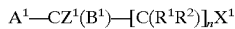

A$^1$—CZ$^1$(B$^1$)—[C(R$^1$R$^2$)]$_n$X$^1$ wherein

A$^1$ is H, HOOC, H$_2$NOC, or —NHOC;

B$^1$ is SH or NHR$^3$;

X$^1$ is H, methyl, SH or NHR$^3$;

Z$^1$ is H or methyl;

R$^1$ and R$^2$ are independently H or lower alkyl;

R$^3$ is H, lower alkyl or —C=O;

n is 0, 1 or 2;

and where B$^1$ is NHR$^3$, X$^1$ is SH, Z$^1$ is H and n is 1 or 2; where X$^1$ is NHR$^3$, B$^1$ is SH, Z$^1$ is H and n is 1 or 2; where B$^1$ is H, A$^1$ is HOOC, H$_2$NOC, or —NHOC, X$^1$ is SH, Z$^1$ is H and n is 0 or 1; where Z$^1$ is methyl, X$^1$ is methyl, A$^1$ is HOOC, H$_2$NOC, or —NHOC,, B$^1$ is SH and n is 0; and wherein the thiol moiety is in the reduced form. In a preferred embodiment, the peptide comprises between 3 and 30 amino acids. Preferred embodiments of the invention comprise linear and cyclic specific binding peptides.

In another embodiment, the invention provides peptide reagents capable of being Tc-99m labeled for imaging sites within a mammalian body comprising a multiplicity of specific binding peptides having an amino acid sequence of 3–100 amino acids, covalently linked to a polyvalent linking moiety, and a Tc-99m binding moiety covalently linked to a plurality of the specific-binding peptides, the polyvalent linker moiety, or both, wherein the Tc-99m binding moiety has formula:

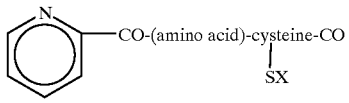

[for purposes of this invention, radiolabel-binding moieties having this structure will be referred to as picolinic acid (Pic)-based moieties] or

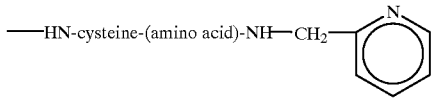

wherein X is H or a protecting group and (amino acid) is any amino acid. For purposes of this invention, radiolabel-binding moieties having this structure will be referred to as picolylamine (Pica)-based moieties. In a preferred embodiment, the amino acid is glycine and X is an acetamidomethyl protecting group. In additional preferred embodiments, the peptide is comprised between 3 and 30 amino acids. Preferred embodiments of the invention comprise linear and cyclic specific binding peptides.

Yet another embodiment of the invention provides peptide reagents capable of being labeled with Tc-99m for imaging sites within a mammalian body, comprising a multiplicity of specific binding peptides having an amino acid sequence of 3–100 amino acids, covalently linked to a polyvalent linking moiety, and a Tc-99m binding moiety covalently linked to the specific-binding peptides, the polyvalent linker moiety, or both, wherein the Tc-99m binding moiety has formula:

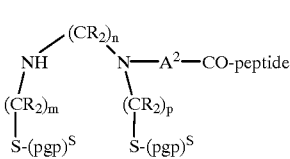

I.

wherein each R can be independently H, CH$_3$ or C$_2$H$_5$; each (pgp)$^S$ can be independently a thiol protecting group or H; m, n and p are independently 2 or 3; A$^2$ is linear or cyclic lower alkyl, aryl, heterocyclyl, combinations or substituted derivatives thereof; and X is peptide; and

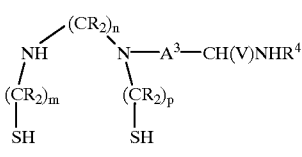

II.

wherein each R is independently H, CH$_3$ or C$_2$H$_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is peptide. [For purposes of this invention, radiolabel-binding moieties having these structures will be referred to as "BAT" moieties]. Preferred embodiments of the invention comprise linear and cyclic specific binding peptides.

Specific-binding peptides provided by the invention include but are not limited to peptides having the following sequences:

(acetyl-F$_D$PRPG)$_2$KGGGCamide (GPRVVERHQSA)$_2$KC$_{Acm}$GC$_{Acm}$amide

[(GPRP)$_2$K]$_2$KC$_{Acm}$GC$_{Acm}$amide

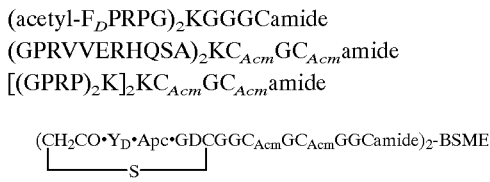

(CC$_{Acm}$GC$_{Acm}$GGRGDS)$_3$-TSEA (GPRPC$_{Acm}$GC$_{Acm}$Camide)$_3$-TSEA (Pic.SC$_{Acm}$SYNRGDSTCamide)$_3$-TSEA (RALVDTLKGGC$_{Acm}$GC$_{Acm}$Camide)$_3$-TSEA (GRGDFC$_{Acm}$GC$_{Acm}$Camide)$_3$-TSEA (Pic.GC$_{Acm}$RALVDTLKFVTQAEGAKCamide)$_3$-TSEA (acetyl-SYNRGDTC$_{Acm}$GC$_{Acm}$Camide)$_3$-DMAB The specific binding peptides of the invention are covalently linked to a polyvalent linking moiety. Polyvalent linking moieties of the invention are comprised of at least 2 identical linker functional groups capable of covalently bonding to specific binding peptides or Tc-99m binding moieties. Preferred linker functional groups are primary or secondary amines, hydroxyl groups, carboxylic acid groups or thiol-reactive groups. In preferred embodiments, the polyvalent linking moieties are comprised of a multiplicity of polyvalent linking moieties covalently linked to form a branched polyvalent linking moiety. The invention also comprises complexes of the peptides of the invention with Tc-99m and methods for radiolabeling the peptides of the invention with Tc-99m. Radiolabeled complexes provided by the invention are formed by reacting the peptides of the invention with Tc-99m in the presence of a reducing agent. Preferred reducing agents include but are not limited to dithionite ion, stannous ion, and ferrous ion. Complexes of the invention are also formed by labeling the peptides of the invention with Tc-99m by ligand exchange of a prereduced Tc-99m complex as provided herein.

The invention also provides kits for preparing the peptides of the invention radiolabeled with Tc-99m. Kits for labeling the peptide of the invention with Tc-99m are comprised of a sealed vial containing a predetermined quantity of a peptide of the invention and a sufficient amount of reducing agent to label the peptide with Tc-99m.

This invention provides methods for preparing peptides of the invention by chemical synthesis in vitro. In a preferred embodiment, peptides are synthesized by solid phase peptide synthesis.

This invention provides methods for using Tc-99m labeled peptides for imaging a site within a mammalian body by obtaining in vivo gamma scintigraphic images. These methods comprise administering an effective diagnostic amount of a Tc-99m radiolabeled peptide of the invention and detecting the gamma radiation emitted by the Tc-99m localized at the site within the mammalian body.

Specific preferred embodiments of the present invention will become evident from the following more detailed description of certain preferred embodiments and the claims.

DETAILED DESCRIPTION OF THE INVENTION

The present invention provides reagents for preparing Tc-99m labeled peptides for imaging target sites within a mammalian body comprising a multiplicity of specific binding peptide having an amino acid sequence of 3–100 amino acids, covalently linked to a polyvalent linking moiety, and a Tc-99m binding moiety covalently linked to the specific-binding peptides, the polyvalent linker moiety, or both.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo—$^{99m}$Tc generator. Other radionuclides known in the prior art have effective half-lives which are much longer (for example, $^{111}$In, which has a half-life of 67.4 h) or are toxic (for example, $^{125}$I).

In the radiolabel binding moieties and peptides covalently linked to such moieties that contain a thiol covalently linked to a thiol protecting groups [(pgp)$^S$] provided by the invention, the thiol-protecting groups may be the same or different and may be but are not limited to:

—CH$_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—CH$_2$-(4-methoxyphenyl);

—CH-(4-pyridyl)(phenyl)$_2$;

—C(CH$_3$)$_3$-9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$-phenyl

Prefereed protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Polyvalent linking moieties are covalently linked to the specific peptides of the invention, the Tc-99m binding moieties, or both. Polyvalent linking moieties provided by the invention are comprised of at least 2 linker functional groups capable of covalently bonding to specific binding peptides or Tc-99m binding moieties. Such functional groups include but are not limited to primary and secondary amines, hydroxyl groups, carboxylic acid groups and thiol reactive groups. Polyvalent linking moieties are comprised of preferably at least three functional groups capable of being covalently linked to specific binding peptides or technetium-99m binding moieties. Preferred polyvalent linking moieties include amino acids such as lysine, homolysine, ornithine, aspartic acid and glutamic acid; linear and cyclic amines and polyamines; polycarboxylic acids; and activated thiols such as di- and tri-maleimides. Also preferred are embodiments wherein the polyvalent linking moieties comprise a multiplicity of polyvalent linking moieties covalently linked to form a branched polyvalent linking moiety. For the purposes of this invention, the term "branched" polyvalent linking moieties is intended to include but are not limited to polyvalent linking moieties having formula:

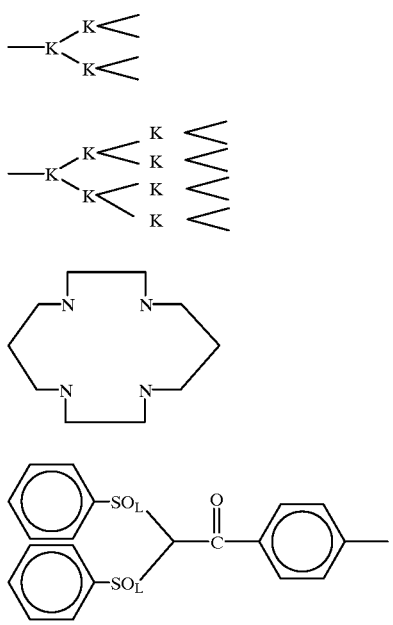

Peptides of the present invention can be chemically synthesized in vitro. Peptides of the present invention can generally advantageously be prepared on an amino acid synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments [e.g., Pic-Gly-Cys(protecting group)-] comprising picolinic acid (Pic-), the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys-chelator are provided in the Examples hereinbelow. This invention provides for the incorporation of these chelators into virtually any peptide, resulting in a radiolabeled peptide having Tc-99m held as neutral complex.

This invention also provides specific-binding small synthetic peptides which incorporate bisamine bisthiol (BAT) chelators which may be labeled with Tc-99m, resulting in a radiolabeled peptide having Tc-99m held as neutral complex.

In forming a complex of radioactive technetium with the peptides of this invention, the technetium complex, preferably a salt of Tc-99m pertechnetate, is reacted with the peptides of this invention in the presence of a reducing agent. Preferred reducing agents are dithionite, stannous and ferrous ions; the most preferred reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of a peptide of the invention to be labeled and a sufficient amount of reducing agent to label the peptide with Tc-99m. Alternatively, the complex may be formed by reacting a peptide of this invention with a preformed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled peptides is provided. The peptides of the invention can be chemically synthesized using methods and means well-known to those with skill in the art and described hereinbelow. Peptides thus prepared are comprised of between 3 and 100 amino acid residues, and are covalently linked to a radiolabel-binding moiety wherein the radiolabel-binding moiety binds a radioisotope. An appropriate amount of the peptide is introduced into a vial containing a reducing agent, such as stannous chloride or a solid-phase reducing agent, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 3 hereinbelow.

Radioactively labeled peptides provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

Technetium-labeled peptides provided by the present invention can be used for visualizing sites in a mammalian body. In accordance with this invention, the technetium-labeled peptides or neutral complexes thereof are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the organ or tumor in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Synthesis of BAT Chelators

1. Synthesis of TMEA [tris(2-maleimidoethyl)amine]

tris(2-aminoethyl)amine (1.49 mL, 10 mmol) dissolved in 50 mL saturated aqueous sodium bicarbonate and cooled in an ice bath, was treated with N-carbomethoxymaleimide (4.808 g, 31 mmol). The mixture was stirred for 30 min on ice and then for another 30 min at room temperature. The mixture was then partitioned between dichloromethane and water, dried over magnesium sulfate, filtered and evaporated to give 3.442 g of product. Reverse phase thin-layer chromatography (RP-TLC) yielded essentially 1 spot ($R_f$=0.63 in 1:1 acetonitrile: 0.5 M sodium chloride). 3.94 mmol (1.817g) of this product was dissolved in 20 mL tetrahydrofuran and 20 mL saturated sodium bicarbonate and mixed for 2 h. The reaction mixture was then partitioned between ethyl acetate and water. The organic phase was washed with saturated sodium chloride, dried over magnesium sulfate, and filtered. The ethyl acetate solution was diluted with hexanes and cooled. Solid TMEA was collected by filtration and dried to a yield of 832 mg. Chemical analysis of the product confirmed its identity as TMEA as follows:

$^1$H NMR (CDCl$_3$): 2.65 (tr. 2 H), 3.45 (tr.2 H). 6.64 (s. 2 H).

$^{13}$C NMR (CDCl$_3$), 35.5, 51.5, 133.9, 170.4.

2. Synthesis of TMEB (4-[1-(2-tolylsulfonylmethyl) ethenylcarbonyl]benzoic acid)

4-(bis-(2-toluenethiomethyl)acetyl)benzoic acid was prepared from 2-thiocresol using the methods of Lawton and co-workers (1990, Bioconjugate Chemistry 1: 36). The identity of the resulting compound was established by chemical analysis as follows:

FABMS: MH$^+$=436.

$^1$H NMR (CDCl$_3$)=2.62 (s, 6H), 3.2–3.4 (m, 4H), 3.94 (d tr, 1H), 7.10–7.26 (m, 8H), 7.64 (d, 2H), 8.07 (d, 2H).

$^{13}$C NMR (CDCl$_3$): 20.2, 34.9, 45.4, 126.5, 126.8, 128.1, 129.9, 130.3, 130.4, 132.9, 133.9, 138.9, 140.5.

To a solution of 4-(bis-(2-toluenethiomethyl)acetyl) benzoic acid (1.865 g, 4.27 mmol) in 50% methanol/water (12.5 mL) was added acetic acid (2.69 mL) followed by 30% hydrogen peroxide (2.61 mL) and disodium tungstate dihydrate (0.187 g, 0.56 mmol). The mixture was stirred overnight and the crude product was filtered off. Recrystallization from methanol/water and reverse-phase HPLC (0.1% CF$_3$COOH/acetonitrile/water) gave TMEB (178 mg). The identity of the resulting compound was established by chemical analysis as follows:

$^1$H NMR (DMSO-d6): 2.68 (s, 3H), 4.56 (s, 2H), 5.95 (s. 1H), 6.27 (s. 1H), 7.37–8.05 (m, 8H).

EXAMPLE 2

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzo-triazol-1-yl)-1,1,3,3-tetramethyluronium hexafluorophosphate/ hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature.

Where appropriate N-terminal acetyl groups were introduced by treating the free N-terminal amino peptide bound to the resin with 20% v/v acetic anhydride in NMP (N-methylpyrrolidinone) for 30 min. Where appropriate 2-chloroacetyl or 2-bromoacetyl groups were introduced either by using the appropriate 2-haloacetic acid as the last residue to be coupled during SPPS, or by treating the N-terminus free amino acid peptide bound to the resin with either the 2-haloacetic acid/diisopropylcarbodiimide/N-hydroxysuccinimide in NMP or the 2-haloacetic anhydride/ diisopropylethylamine in NMP.

Where appropriate, HPLC-purified 2-haloacetylated peptides were cyclized by stirring an 0.1–1.0 mg/mL solution in phosphate or bicarbonate buffer (pH 8.0) containing 0.5–1.0 mM EDTA for 4–48 h followed by acidification with acetic acid, lyophilization and HPLC purification.

Where appropriate, DMAB adducts were prepared by reacting single thiol-containing peptides (10 to 100 mg/mL in DMF) with 0.5 molar equivalents of TMEB (described in Example 1) and 1 molar equivalent of triethanolamine at room temperature for approximately 12 to 18 hours. DMF was then removed in vacuo and the product purified by HPLC.

Where appropriate, TSEA adducts were prepared by reacting single thiol-containing peptides (10 to 100 mg/mL in DMF) with 0.33 molar equivalents of TMEA [tris(2-maleimidoethyl)amine] with or without 1 molar equivalent of triethanolamine at room temperature for approximately 7 hours to 5 days. DMF was then removed in vacuo and the product purified by HPLC.

Where appropriate, BSME adducts were prepared by reacting single thiol-containing peptides (5 to 50 mg/mL in 50 mM sodium phosphate buffer, pH 8) with 0.5 molar equivalents of BMME (bis-maleimidomethylether) predissolved in acetonitrile at room temperature for approximately 1 to 18 hours. The solution was concentrated and the product was product by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 3

A General Method for Radiolabeling with Tc-99m 0.1 mg of a peptide prepared as in Example 2 was dissolved in 0.1 mL of water or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature or at 100° C. for 15–30 min and then filtered through a 0.2 μm filter.

The Tc-99m labeled peptide purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 2 using the method described herein.

| | FABMS MH+ | Radiochemical Yield (%)* | HPLC $R_T$(min)** |
|---|---|---|---|
| (acetyl-$F_D$PRPG)$_2$KGGGCamide | 1613 | 98[2] | 17.4 |
| (GPRVVERHQSA)$_2$KC$_{Acm}$GC$_{Acm}$amide | 2986 | 99[3] | 16.0 |
| [(GPRP)$_2$K]$_2$KC$_{Acm}$GC$_{Acm}$amide | 2437 | 100[3] | 16.3 |
| 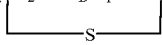 | 3021 | ND | ND |
| (CC$_{Acm}$GC$_{Acm}$GGRGDS)$_3$-TSEA | ND | 82[1] | 10.4 |
| (GPRPC$_{Acm}$GC$_{Acm}$Camide)$_3$-TSEA | 3189 | 93[1] | 10.0 |
| (Pic.SC$_{Acm}$SYNRGDSTCamide)$_3$-TSEA | 4489 | 99[1] | 10.4, 11.2 |
| (RALVDTLKGGC$_{Acm}$GC$_{Acm}$Camide)$_3$-TSEA | 4998 | 95[2] | 13.4, 13.7 |
| (GRGDFC$_{Acm}$GC$_{Acm}$Camide)$_3$-TSEA | 3561 | ND | ND |
| (Pic.GC$_{Acm}$RALVDTLKFVTQAEGAKCamide)$_3$-TSEA | 7244 | 98[4] | 18.3, 19.0 |
| (acetyl-SYNRGDTC$_{Acm}$GC$_{Acm}$Camide)$_2$-DMAB | 3087 | ND | ND |

*Superscripts refer to the following labeling conditions:
[1]The peptide is dissolved in 50 mM potassium phosphate buffer (pH 7.4) and labeled at 100° C.
[2]The peptide is dissolved in water and labeled at room temperature.
[3]the peptide is dissolved in a 50:50 mixture comprising 50 mM potassium phosphate buffer (pH 7.4) and absolute ethanol and labeled at 100° C.
**HPLC methods (indicated by superscript after $R_T$):
general:
solvent A = 0.1% CF3COOH/H$_2$O
solvent B$_{90}$ = 0.1% CF$_3$COOH/90% CH$_3$CN/H$_2$O
solvent flow rate = 1 mL/min
Vydak column = Vydak 218TP54 RP-18, 5μ × 220 mm × 4.6 mm analytical column with guard column
Conditions: 100% A to 100% B$_{90}$ in 10 min
Single-letter abbreviations for amino acids can be found in G. Zubay, Biochemistry (2d. ed.), 1988 (MacMillen Publishing: New York) p. 33;
Pic = picolinoyl (pyridine-2-carbonyl);
Acm = acetamidomethyl;
Apc = L-[S-(3-aminopropyl)cysteine;
$F_D$ = D-phenylalanine;
$Y_D$ = D-tyrosine;
BSME = bis-succinimdylmethylether;
DMAB = 4-(2,2-dimethylacetyl)benzoic acid;
TSEA = tris(succinimidylethyl)amine
Peptides are linked to BSME, DMAB or TSEA linkers via the free thiol moiety of the unprotected cysteine residue (C) in each peptide.

It should be understood that the foregoing disclosure emphasizes certain specific embodiments of the invention and that all modifications or alternatives equivalent thereto are within the spirit and scope of the invention as set forth in the appended claims.

What is claimed is:

1. A radiolabeled complex comprising:
   a) technetium-99m; and
   b) a reagent comprising:
      i) a multiplicity of synthetically prepared, specific-binding peptides, each peptide having an amino acid sequence of 3 to 100 amino acids,
      ii) a polyvalent linker covalently linked to each peptide, and
      iii) a technetium-99m binding moiety covalently linked to a specific site on each peptide.

2. A method for labeling a reagent by ligand exchange, wherein the reagent comprises:
   i) a multiplicity of synthetically prepared, specific-binding peptides, each peptide having an amino acid sequence of 3 to 100 amino acids,
   ii) a polyvalent linker covalently linked to each peeptide, and
   iii) a technetium-99m binding moiety covalently linked to a specific site on each peptide;
the method comprising the step of combining the reagent with a prereduced technetium-99m complex.

3. A method for labeling a reagent comprising:
   i) a multiplicity of synthetically prepared, specific-binding peptides, each peptide having an amino acid sequence of 3 to 100 amino acids,
   ii) a polyvalent linker covalently linked to each peptide, and
   iii) a technetium-99m binding moiety covalently linked to a specific site on each peptide;

the method comprising the step of reacting the reagent with technetium-99m in the presence of a reducing agent.

4. The method of claim 3, wherein the reducing agent is selected from the group consisting of a dithionite ion, a stannous ion and a ferrous ion.

5. A radiolabeled complex comprising technetium-99m and a reagent selected from the group consisting of:

(acetyl-F$_D$PRPG)$_2$KGGGCamide,
(GPRVVERHQSA)$_2$KC$_{Acm}$GC$_{Acm}$amide,
{(GPRP)$_2$K}$_2$KC$_{Acm}$GC$_{Acm}$amide,

[(CH$_2$CO·Y$_D$·Apc·GDCGGC$_{Acm}$GC$_{Acm}$GGCamide)$_2$-BSME,]
\—S—/

(CC$_{Acm}$GC$_{Acm}$GGRGDS)$_3$-TSEA,
(GPRPC$_{Acm}$GC$_{Acm}$Camide)$_3$-TSEA,
(Pic.SC$_{Acm}$SYNRGDSTCamide)$_3$-TSEA,
(RALVDTLKGGC$_{Acm}$GC$_{Acm}$Camide)$_3$-TSEA,
(GRGDFC$_{Acm}$GC$_{Acm}$Camide)$_3$-TSEA,
(Pic.GC$_{Acm}$RALVDTLKFVTQAEGAKCamide)$_3$-TSEA, and
(acetyl-SYNRGDTC$_{Acm}$GC$_{Acm}$Camide)$_2$-DMAB.

6. A radiolabeled complex comprising:
a) technetium-99m; and
b) a reagent comprising:
(i) a polyvalent linker;
(ii) a multiplicity of synthetically prepared, specific-binding peptides, each peptide having an amino acid sequence of 3 to 100 amino acids and being covalently linked to said linker, and
(iii) a technetium-99m binding moiety covalently linked to said linker.

7. A method for labeling a reagent by ligand exchange, wherein the reagent comprises:
(i) a polyvalent linker;
(ii) a multiplicity of synthetically prepared, specific-binding peptides, each peptide having an amino acid sequence of 3 to 100 amino acids and being covalently linked to said linker; and
(iii) a technetium-99m binding moiety covalently linked to said linker;
the method comprising the step of combining the reagent with a prereduced technetium-99m complex.

8. A method for labeling a reagent comprising:
(i) a polyvalent linker;
(ii) a multiplicity of synthetically prepared, specific-binding peptides, each peptide having an amino acid sequence of 3 to 100 amino acids and being covalently linked to said linker, and
(iii) a technetium-99m binding moiety covalently linked to said linker;
the method comprising the step of reacting the reagent with technetium-99m in the presence of a reducing agent.

9. A radiolabeled complex comprising:
a) technetium-99m; and
b) a reagent comprising:
i) a multiplicity of synthetically prepared, specific-binding peptides, each peptide having an amino acid sequence of 3 to 100 amino acids;
ii) a branched polyvalent linker covalently linked to a specific site on each peptide; and
iii) a technetium-99m binding moiety covalently linked to the linker.

10. A method for labeling a reagent by ligand exchange, wherein the reagent comprises:
i) a multiplicity of synthetically prepared, specific-binding peptides, each peptide having an amino acid sequence of 3 to 100 amino acids;
ii) a branched polyvalent linker covalently linked to a specific site on each peptide; and
iii) a technetium-99m binding moiety covalently linked to the linker,
the method comprising the step of combining the reagent with a prereduced technetium-99m complex.

11. A method for labeling a reagent comprising:
i) a multiplicity of synthetically prepared, specific-binding peptides, each peptide having an amino acid sequence of 3 to 100 amino acids;
ii) a branched polyvalent linker covalently linked to a specific site on each peptide;
iii) a technetium-99m binding moiety covalently linked to the linker,
the method comprising the step of reacting the reagent with technetium-99m in the presence of a reducing agent.

12. A radiolabeled complex comprising:
a) technetium-99m; and
b) a reagent comprising:
i) a multiplicity of synthetically prepared, specific-binding peptides, each peptide having an amino acid sequence of 3 to 100 amino acids;
ii) a technetium-99m binding moiety covalently linked to a specific site on each peptide; and
iii) a polyvalent linker covalently linked to each technetium-99m binding moiety.

13. A method for labeling a reagent by ligand exchange, wherein the reagent comprises:
i) a multiplicity of synthetically prepared, specific-binding peptides, each peptide having an amino acid sequence of 3 to 100 amino acids;
ii) a technetium-99m binding moiety covalently linked to a specific site on each peptide; and
iii) a polyvalent linker covalently linked to each technetium-99m binding moiety;
the method comprising the step of combining the reagent with a prereduced technetium-99m complex.

14. A method for labeling a reagent comprising:
i) a multiplicity of synthetically prepared, specific-binding peptides, each peptide having an amino acid sequence of 3 to 100 amino acids;
ii) a technetium-99m binding moiety covalently linked to a specific site on each peptide; and
iii) a polyvalent linker covalently linked to each technetium-99m binding moiety;
the method comprising the step of reacting the reagent with technetium-99m in the presence of a reducing agent.

15. A method of making a technetium-99m labeled peptide comprising the step of combining

with technetium-99m in the presence of stannous ions.

16. A method of making a technetium-99m labeled peptide by ligand exchange comprising the step of combining (CH₂CO•Y_D Apc•GDCGGC_Acm GC_Acm GGCamide)₂-BSME
        \\_S⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯/ with a prereduced technetium-99m complex.

17. The complex of any of claims 1, 6, 9 or 12, wherein the linker comprises at least two identical functional groups.

18. The complex of claim 17, wherein the functional groups are selected from the group consisting of primary amines, secondary amines, hydroxyl groups, carboxylic acid groups, and thiol-reactive groups.

19. A complex according to any of claims 1, 6, or 12, wherein the linkers form a covalently linked, branched polyvalent linking moiety.

20. The complex of any of claims 1, 6, 9, or 12, wherein the technetium-99m binding moiety is selected from the group consisting of:

$$C(pgp)^S-(aa)-C(pgp)^S \qquad \text{I.}$$

wherein c(pgp)$^S$ is a cysteine having a protected thiol group and (aa) is an amino acid;

a technetium-99m binding moiety comprising a single thiol having a formula $$A^1-CZ^1(B^1)-[C(R^1R^2)]_n-X^1 \qquad \text{II.}$$

wherein
- $A^1$ is H, HOOC, H₂NOC, or —NHOC;
- $B^1$ is SH or NHR³;
- $X^1$ is H, methyl, SH or NHR³;
- $Z^1$ is H or methyl;
- $R^1$ and $R^2$ are independently H or lower alkyl;
- $R^3$ is H, lower alkyl or —C=O;
- n is 0, 1 or 2;

and where $B^1$ is NHR³, $X^1$ is SH, $Z^1$ is H and n is 1 or 2; where $X^1$ is NHR³, $B^1$ is SH, $Z^1$ is H and n is 1 or 2; where $B^1$ is H, $A^1$ is HOOC, H₂NOC, or —NHOC, $X^1$ is SH, $Z^1$ is H and n is 0 or 1;
where $Z^1$ is methyl, $X^1$ is methyl, $A^1$ is HOOC, H₂NOC, or —NHOC, $B^1$ is SH and n is 0;
and wherein the thiol moiety is in the reduced form;

(pyridyl)—CO-(amino acid)-cysteine-CO— III.
                              |
                              SX² wherein
- $X^2$=H or a protecting group;
- (amino acid)=any amino acid;

—HN-cysteine-(amino acid)-HN—CH₂—(pyridyl) IV.
                  |
                  SX² wherein
- $X^2$=H or a protecting group;
- (amino acid)=any amino acid;

```
         (CR₂)n
        /
      NH        N—A²—CO-peptide
      |         |
      (CR₂)m   (CR₂)p
      |         |
      S-(pgp)^S S-(pgp)^S
```
V.

wherein
- each R is independently H, CH₃ or C₂H₅;
- each (pgp)$^S$ is independently a thiol protecting group or H;
- m, n and p are independently 2 or 3;
- $A^2$=linear or cyclic lower alkyl, aryl, heterocyclyl, or a combination thereof;

and

```
         (CR₂)n
        /
      NH        N—A³—CH(V)NHR⁴
      |         |
      (CR₂)m   (CR₂)p
      |         |
      SH        SH
```
VI.

wherein
- each R is independently H, CH₃ or C₂H₅;
- m, n and p are independently 2 or 3;
- $A^3$=linear or cyclic lower alkyl, aryl, heterocyclyl, or a combination thereof;
- V=H or —CO-peptide;
- $R^4$=H or peptide;

and wherein when V=H, $R^4$=peptide and when $R^4$=H, V=—CO-peptide.

21. The complex of any of claims 1, 6, 9, or 12, wherein the technetium-99m binding moiety is selected from the group consisting of a protected thiol-containing moiety, a single thiol containing complexing moiety, a picolinic acid-based moiety, a picolylamine-containing moiety, and a bisamine bisthiol-containing moiety.

22. The complex of any of claims 1, 6, 9, or 12, wherein the linker comprises an amino acid selected from the group consisting of lysine, homocysteine, ornithine, aspartic acid, and glutamic acid.

\* \* \* \* \*